(12) United States Patent
Yost et al.

(10) Patent No.: US 6,761,695 B2
(45) Date of Patent: Jul. 13, 2004

(54) METHOD AND APPARATUS FOR NON-INVASIVE MEASUREMENT OF CHANGES IN INTRACRANIAL PRESSURE

(75) Inventors: William T. Yost, Newport News, VA (US); John H. Cantrell, Jr., Williamsburg, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 143 days.

(21) Appl. No.: 10/094,023

(22) Filed: Mar. 7, 2002

(65) Prior Publication Data

US 2003/0171693 A1 Sep. 11, 2003

(51) Int. Cl.[7] .................................................. A61B 5/00
(52) U.S. Cl. ...................................................... 600/561
(58) Field of Search ................................ 600/561, 587, 600/438, 451

(56) References Cited

U.S. PATENT DOCUMENTS

| | | | |
|---|---|---|---|
| 4,971,061 A | | 11/1990 | Kageyama et al. |
| 4,984,567 A | * | 1/1991 | Kageyama et al. .......... 600/438 |
| 5,214,955 A | | 6/1993 | Yost et al. |
| 5,388,583 A | * | 2/1995 | Ragauskas et al. .......... 600/451 |
| 5,617,873 A | | 4/1997 | Yost et al. |
| 5,951,476 A | | 9/1999 | Beach |
| 6,117,089 A | | 9/2000 | Sinha |
| 6,210,346 B1 | | 4/2001 | Hall et al. |
| 6,231,509 B1 | | 5/2001 | Johnson et al. |
| 6,264,611 B1 | | 7/2001 | Ishikawa et al. |
| 6,413,227 B1 | | 7/2002 | Yost et al. |
| 6,475,147 B1 | | 11/2002 | Yost et al. |
| 6,589,189 B2 | * | 7/2003 | Meyerson et al. .......... 600/561 |
| 2003/0191409 A1 | | 10/2003 | Yost et al. |
| 2003/0191410 A1 | | 10/2003 | Yost et al. |
| 2003/0191411 A1 | | 10/2003 | Yost et al. |

FOREIGN PATENT DOCUMENTS

WO    WO 00/68647    11/2000

OTHER PUBLICATIONS

Toshiaki Ueno et al., "Effects of Whole Body Tilting on Intracranial Pressure Dynamics," Sep. 2002.
Toshiaki Ueno et al., "Noninvasive Measurement of Pulsatile Intracranial Pressure Using Ultrasound," Acta Neurochir, p. 66–69, (Dec. 23, 1998 ).

* cited by examiner

*Primary Examiner*—Eric F. Winakur
(74) *Attorney, Agent, or Firm*—Helen M. Galus

(57) ABSTRACT

A method and apparatus for measuring intracranial pressure. In one embodiment, the method comprises the steps of generating an information signal that comprises components (e.g., pulsatile changes and slow changes) that are related to intracranial pressure and blood pressure, generating a reference signal comprising pulsatile components that are solely related to blood pressure, processing the information and reference signals to determine the pulsatile components of the information signal that have generally the same phase as the pulsatile components of the reference signal, and removing from the information signal the pulsatile components determined to have generally the same phase as the pulsatile components of the reference signal so as to provide a data signal having components wherein substantially all of the components are related to intracranial pressure.

12 Claims, 5 Drawing Sheets

METHOD AND APPARATUS FOR NON-INVASIVE MEASUREMENT OF CHANGES IN INTRACRANIAL PRESSURE

ORIGIN OF THE INVENTION

The invention described herein was made by an employee of the United States Government and may be used by or for the Government for governmental purposes without the payment of any royalties thereon or therefor.

BACKGROUND OF THE INVENTION

1. Technical Field of the Invention

The present invention relates broadly to the field of apparatuses and methods for measuring intracranial pressure.

2. Related Art and Problems to be Solved

Monitoring intracranial pressure (ICP) is of significant diagnostic and post-operative importance for patients with cranial injuries, pathologies, or other conditions that may affect the pressure of the subarachnoidal fluid around the brain, and for patients who have undergone brain surgery.

Many known methods and techniques are invasive and thus, can be very painful, and possibly harmful to the eardrum. Other known methods require absolute calibration which can require bolus injection into the column surrounding the spinal cord, head titling procedures, and determination of blood volume input and output. Some of these requirements are impractical and invasive. Still other known techniques and apparatuses use ultrasonic power, which may be harmful to the patient, in conjunction with extensive algorithms. Furthermore, the accuracy of many of the known algorithms as well as the analysis of the ultrasonic waveforms can be questionable.

Accordingly, it is an object of the present invention to provide a method and apparatus for measuring ICP that solves the problems and cures the deficiencies of the prior art methods, apparatuses and techniques.

Other objects and advantages of the present invention will in part be obvious and will in part be apparent from the specification.

SUMMARY OF THE INVENTION

The present invention is directed to a method and apparatus for measuring intracranial pressure. In at least one embodiment, the instrument can utilize two signals, information and reference, to produce an accurate measurement of changes in ICP. The information signal can include the sum of changes in ICP due to changes in average cranial pressure and changes due to the expansion and relaxation of blood vessels within the brain. The reference signal is taken from a point on the body where the signal consists of essentially changes in blood pressure only. The reference signal gives one the ability to calibrate the information signal because the pulsatile component of the information signal is a scaled replica of the reference signal.

In at least one embodiment, the method comprises the steps of generating an information signal that comprises pulsatile components that are related to intracranial pressure and blood pressure, generating a reference signal comprising pulsatile components that are solely related to blood pressure, processing the information and reference signals to determine the pulsatile components of the information signal that have generally the same phase as the pulsatile components of the reference signal, and removing from the information signal the pulsatile components determined to have generally the same phase as the pulsatile components of the reference signal so as to provide a data signal having pulsatile components wherein substantially all of the pulsatile components are related to intracranial pressure.

In at least one embodiment, the apparatus of the present invention comprises an apparatus for measuring changes in intracranial pressure, comprising a first measuring device for generating an information signal that comprises components (e.g. pulsatile changes and slow changes) that are related to intracranial pressure and blood pressure, a second measuring device for generating a reference signal comprising pulsatile components that are solely related to blood pressure, a processor for processing the information and reference signals to determine the pulsatile components of the information signal that have generally the same phase as the pulsatile components of the reference signal, and a circuit for removing from the information signal the pulsatile components determined to have generally the same phase as the pulsatile components of the reference signal so as to provide a data signal having components wherein substantially all of the components are related to intracranial pressure.

BRIEF DESCRIPTION OF THE DRAWINGS

The features of the invention are believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DETAILED DESCRIPTION OF THE INVENTION

Figure 2:
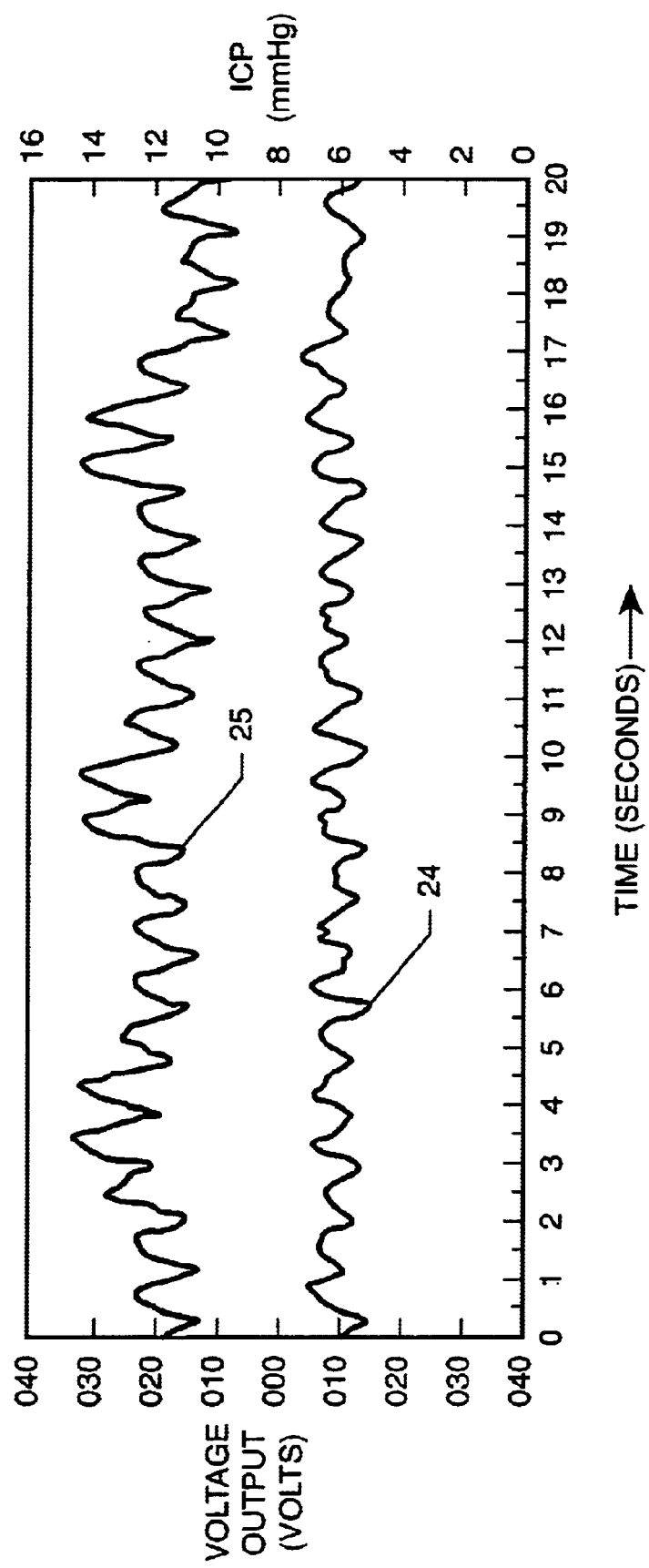
FIG. 2 is a chart showing true and measured ICP waveforms as a function of time.
Figure 3:
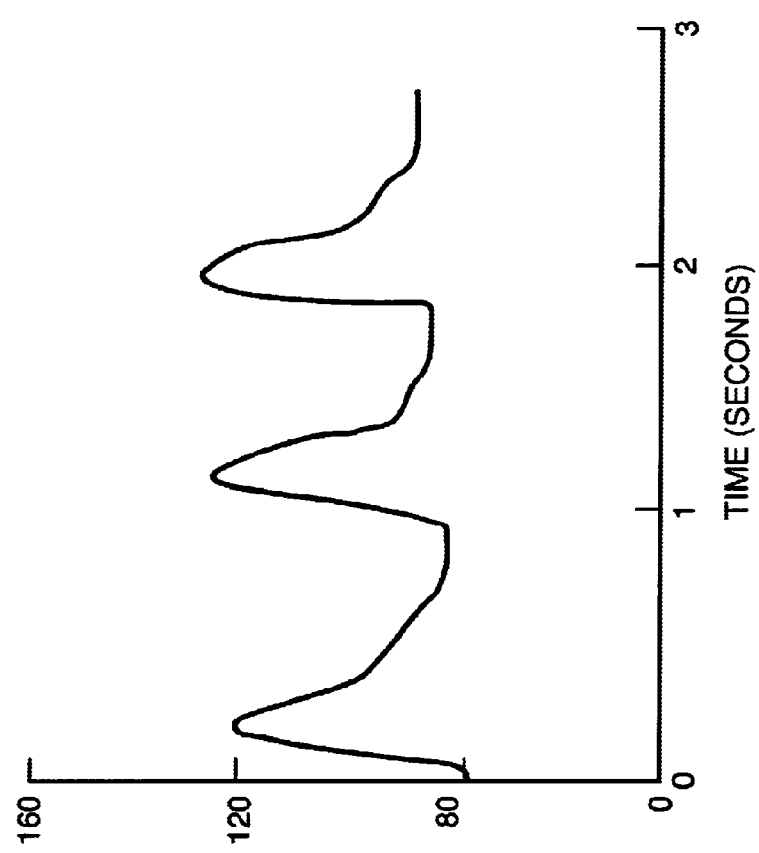
FIG. 3 is a chart illustrating a typical blood pressure waveform as a function of time.

In describing the embodiments of the present invention, reference will be made herein to FIGS. 1-3 of the drawings in which like numerals refer to like features of the invention.

Figure 1:
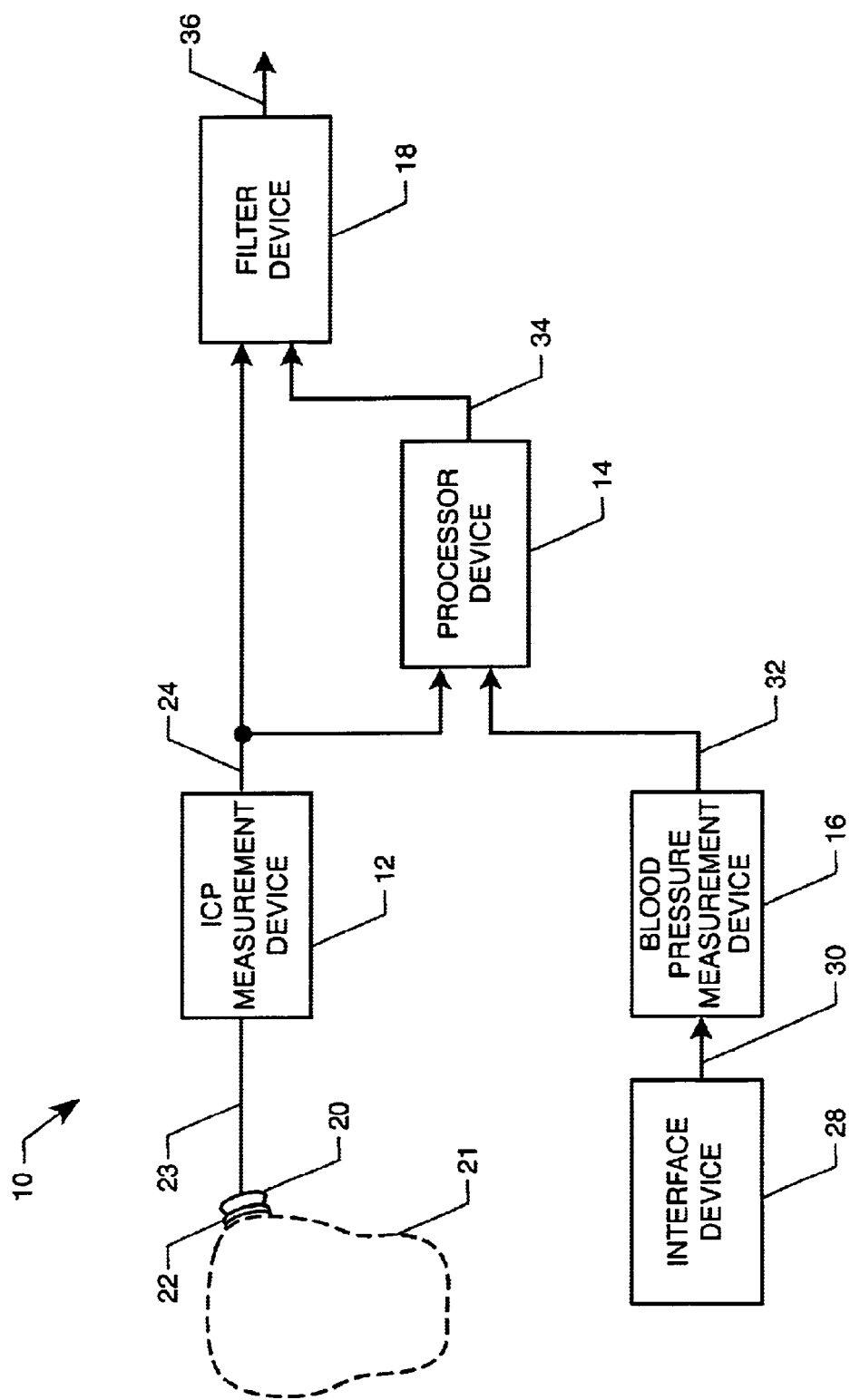
FIG. 1 is a block diagram of an apparatus of the present invention.

Referring now to FIG. 1, there is shown an apparatus 10 of the present invention. Apparatus 10 generally comprises measurement device 12, processing device 14, blood pressure measurement device 16 and filter circuit 18. Apparatus 10 also includes transducer 20 that is configured to be ultrasonically connected to a patent's skull 21 (shown in phantom), for example, via a gel pad 22. Transducer 20 receives acoustic signals from skull 21 which are carried, for example, by wire or cable 23 and inputted into measurement device 12.

Measurement device 12 is configured to generate information signal 24 that comprises components that are related to intracranial pressure and blood pressure. Specifically, information signal 24 includes pulsatile components that represent the expansion and contraction of the skull that is in step with the blood pressure systolic/diastolic variations in the arteries as shown in FIG. 3. In one embodiment, measurement device 12 is configured as a constant frequency pulsed phase-locked loop (CFPPLL) described in commonly owned U.S. Pat. No. 5,214,955, the disclosure of which is herein incorporated by reference as if set forth in its entirety. In an alternate embodiment, measurement device 12 is configured as the measurement device described in commonly owned U.S. Pat. No. 5,617,873, the disclosure of which is herein incorporated by reference as if set forth in its entirety, and indicated by numeral 30 therein.

In one embodiment, measurement device 12 is configured to output signal 24. This is illustrated in FIG. 2 wherein there is shown a chart of ICP versus time. In this example, signal 25 is the true ICP while signal 24, discussed above, is outputted by ICP measurement device 12. Referring again to FIG. 1, apparatus 10 further includes blood pressure interface device 28 which detects signals, such as acoustic signals, related to a patient's blood pressure. Interface device 28 can be configured as a sphygmomanometer or any other suitable device that can be removably attached to a patient's body. Interface device 28 outputs signals, for example acoustic signals 30, for input into blood pressure measurement device 16. In response, blood pressure measurement device 16 outputs signal 32 that comprises pulsatile components that are directly related to the patient's blood pressure. Signal 32 functions as a reference signal and is inputted into processor 14 along with information signal 24. For example, in another embodiment, interface device 28 can be a pressure sensor, such as a blood pressure cuff, then measurement device 16 could be a pressure sensor and associated circuitry to convert the pressure signal into a properly scaled electrical signal 32.

Processor 14 processes information signal 24 and reference signal 32 to determine the pulsatile components of information signal 24 that have generally the same phase as the pulsatile components of reference signal 32. Processor 14 includes phase-adjustment circuitry (not shown) to compensate for any difference in blood pressure phase between the point of blood pressure measurement, e.g. patient's arm, and the blood pressure within the patient's brain. Processor 14 outputs signal 34 which represents the components of information signal 24 that are in phase with the reference signal 32.

In one embodiment, processor 14 is configured as a commercially available lock-in amplifier which includes phase adjustment circuitry described in the foregoing description. The lock-in amplifier outputs signal 34 which was described in the foregoing description. In such an embodiment, the lock-in amplifier also outputs a quadrature signal (not shown) which represents the pulsatile components of information signal 24 that are out of phase with the pulsatile components of reference signal 32. The characteristics of the quadrature signal respond to biologically significant relaxation processes.

In the shown embodiment, information signal 24 and signal 34 are inputted into filter circuit 18. Filter circuit 18 removes the pulsatile components of signal 34 from information signal 24. Filter circuit 18 outputs scaled signal 36 which represents the average components that are only related to intracranial pressure. Signal 36 does not contain any pulsatile components that are related to blood pressure. For example, in one embodiment, signal 36 is a slowly varying voltage having an amplitude that represents the expansion/contraction factor of the skull. Filter circuit 18 can take a variety of forms, for example, in one embodiment, filter circuit 18 is configured as a differential amplifier that effects subtraction of the pulsatile components in signal 34 from information signal 24.

Figure 1A:
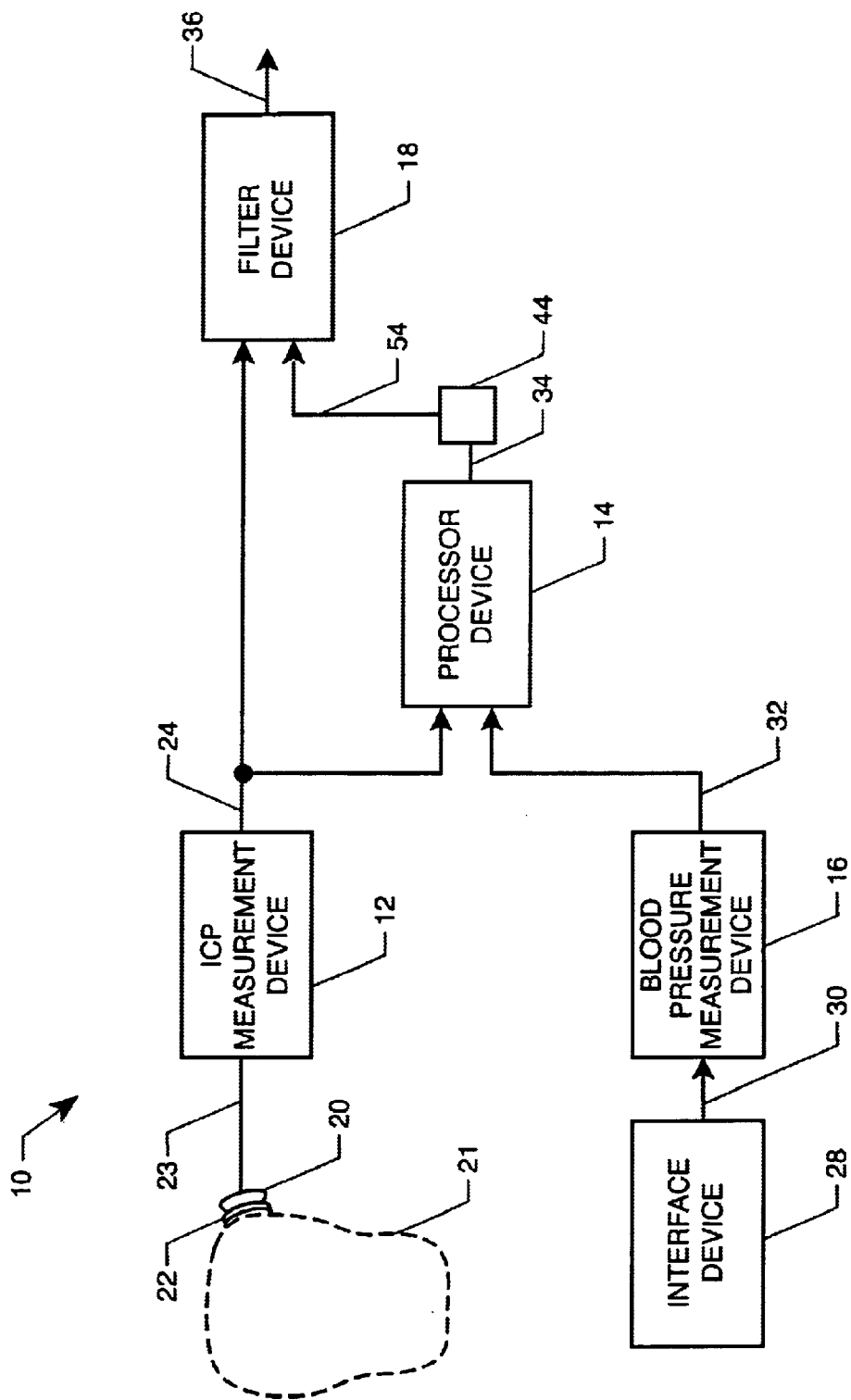
FIG. 1A is a block diagram of another embodiment of an apparatus of the present invention.
Figure 2A:
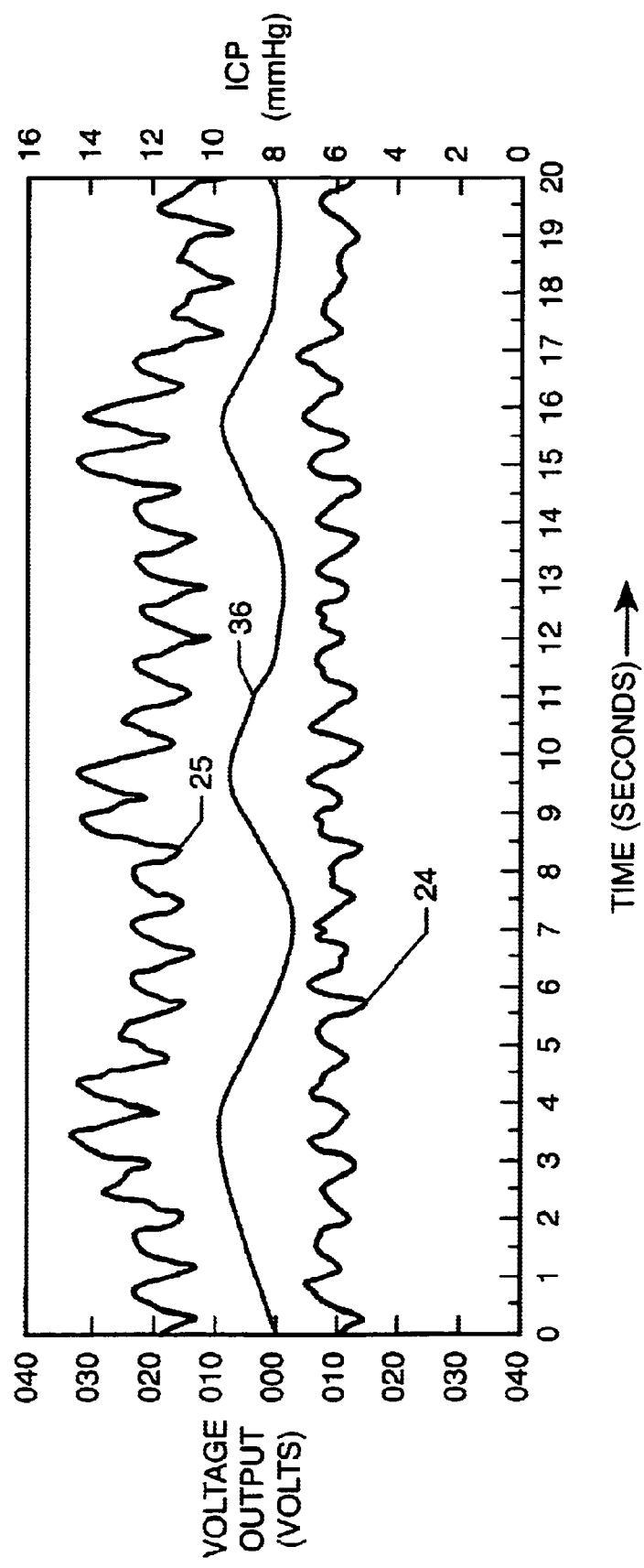
FIG. 2A represents a comparison of various signals described herein.

FIG. 2A shows a comparison of an ICP pressure 25, an information signal 24, and an output signal 36. Signal 36 is the result of subtracting signal 32 (see FIG. 3) from the information signal 24, and filtering with filter device 18. In an alternate embodiment, apparatus 10 includes a blood vessel dynamic average compliance compensator 44, to compensate for the blood vessel dynamic average compliance within the patient's brain. In such an embodiment, the aforesaid compensator receives and process signal 34 and then outputs a processed scaled signal 54 that is inputted into filter circuit 18 (see FIG. 1A). For example, in at least one embodiment, the compliance compensator 44 can include a variable gain amplifier which can be set at a predetermined gain to compensate for the difference in the blood vessel compliance between the brain's blood vessels and the blood vessels at the point where the reference signal is measured. In at least one embodiment, the compliance compensator 44 can be part of the processor device 14. In another embodiment, as shown in FIG. 1A, compliance compensator 44 can be a separate component.

In alternate embodiments, processor 14 and filter circuit 18 can be replaced by other devices or mechanisms. For example, a lock-in amplifier or a double balanced mixer followed by a low-pass filter could be used. In another alternate embodiment, a computer or microprocessor can be used in place of processor 14 and filter 18. In such an embodiment, the computer or microprocessor can implement a program having algorithms that effect signal averaging, Fourier Transforms, etc. Thus, in such an embodiment, signal 36 is generated as a result of numerical manipulation of the information contained in information signal 24 and reference signal 32.

The method and apparatus of the present invention can:
a) non-invasively determine changes in intracranial pressure;
b) monitor blood pressure dynamics to assure adequate supply of nutrients to the brain in cases of compromised blood supply to the brain;
c) be used with tomographic imaging equipment to determine local circulation within the brain; and
d) monitor hemodynamics within the brain (i.e. monitor blood-gas effects on ICP to assure adequate oxygen, etc.)

The principles, embodiments and modes of operation of the present invention have been described in the foregoing specification. The invention which is intended to be protected herein should not, however, be construed as limited to the particular forms disclosed, as these are to be regarded as illustrative rather than restrictive. Variations in changes may be made by those skilled in the art without departing from the spirit of the invention. Accordingly, the foregoing detailed description should be considered exemplary in nature and not limited to the scope and spirit of the invention as set forth in the attached claims.

Thus, having described the invention, what is claimed is:

1. A method for measuring changes in intracranial pressure, comprising:
   generating an information signal that comprises components that are related to intracranial pressure and blood pressure;
   generating a reference signal comprising pulsatile components that are solely related to blood pressure;
   processing the information and reference signals to determine the pulsatile components of the information signal that have generally the same phase as the pulsatile components of the reference signal; and removing from the information signal the pulsatile components determined to have generally the same phase as the pulsatile components of the reference signal so as to provide a data signal having components wherein substantially all of the components are related to intracranial pressure.

2. The method according to claim 1 wherein the step of generating the information signal comprises the step of acquiring a signal proportional to changes in ICP.

3. The method according to claim 1 wherein the step of generating the reference signal comprises the step of measuring a patient's blood pressure.

4. The method according to claim 1 wherein the removing step comprises subtracting from the information signal the pulsatile components determined to have generally the same phase as the pulsatile components of the reference signal.

5. The method according to claim 1 wherein the processing step further comprises the step of processing the pulsatile components that are determined to have generally the same phase as the pulsatile components of the reference signal so as to compensate for blood vessel dynamic compliance.

6. An apparatus for measuring changes in intracranial pressure, comprising:
   a first measuring device for generating an information signal that comprises components that are related to intracranial pressure and blood pressure;
   a second measuring device for generating a reference signal comprising pulsatile components that are solely related to blood pressure;
   a processor for processing the information signal and reference signal to determine the pulsatile components of the information signal that have generally the same phase as the pulsatile components of the reference signal; and
   a circuit for removing from the information signal the pulsatile components determined to have generally the same phase as the pulsatile components of the reference signal so as to provide a data signal having components wherein substantially all of the components are related to intracranial pressure.

7. The apparatus according to claim 6 further including a transducer connected to the first measuring device and configured to have a surface configured for placement upon a patient's skull.

8. The apparatus according to claim 6 wherein the first measuring device comprises a constant frequency pulse phase-locked loop.

9. The apparatus according to claim 6 further including an interface device electrically connected to the second measuring device, the interface device being configured so as to be removably attached to a patient and to receive acoustic signals related to the patient's blood pressure.

10. The apparatus according to claim 6 wherein the circuit is configured to subtract from the information signal the pulsatile components determined to have generally the same phase as the pulsatile components of the reference signal.

11. The apparatus according to claim 6 wherein the processor comprises a lock-in amplifier.

12. The apparatus according to claim 6 wherein the processor is configured to process the pulsatile components that are determined to have generally the same phase as the pulsatile components of the reference signal so as to compensate for blood vessel dynamic compliance.

* * * * *